US007316810B1

(12) United States Patent
Preuilh et al.

(10) Patent No.: US 7,316,810 B1
(45) Date of Patent: Jan. 8, 2008

(54) FOAMING COMPOSITION FOR WASHING AND TREATING HAIR AND/OR SCALP BASED ON AN ACTIVE PRINCIPLE

(75) Inventors: Isabelle Preuilh, Le Cannet (FR); Anne-Emmanuelle Guise, Rouen (FR); Nathalie Willcox, Le Rouret (FR)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 09/709,477

(22) Filed: Nov. 13, 2000

Related U.S. Application Data

(63) Continuation of application No. PCT/FR99/01452, filed on Jun. 17, 1999.

(30) Foreign Application Priority Data

Jun. 19, 1998 (FR) ................... 98 07802

(51) Int. Cl.
*A61Q 5/02* (2006.01)
*A01N 37/36* (2006.01)
*A01N 45/00* (2006.01)
*A61K 31/56* (2006.01)

(52) U.S. Cl. ............... 424/70.1; 424/401; 514/164; 514/168; 514/171; 514/852

(58) Field of Classification Search ........... 424/401, 424/70.1–74; 514/168, 169, 171, 852, 164
See application file for complete search history.

(56) References Cited

U.S. PATENT DOCUMENTS

| 3,984,544 A | * | 10/1976 | Casmer et al. ........... 424/243 |
| 4,235,898 A | * | 11/1980 | Watanabe et al. ......... 514/188 |
| 4,329,334 A | * | 5/1982 | Su et al. ............... 424/70.19 |
| 4,663,069 A | * | 5/1987 | Llenado ................. 510/126 |
| 4,722,837 A | | 2/1988 | Cameron |
| 4,835,148 A | | 5/1989 | Barford et al. |
| 4,853,379 A | | 8/1989 | Shroot |
| 4,894,480 A | * | 1/1990 | Aig et al. ................ 568/11 |
| 4,973,468 A | * | 11/1990 | Chiang et al. ........... 424/449 |
| 5,352,437 A | | 10/1994 | Nakagawa et al. |
| 5,378,731 A | * | 1/1995 | Andrews et al. ......... 514/552 |
| 5,631,003 A | * | 5/1997 | Mueller et al. ......... 424/70.31 |
| 5,653,970 A | * | 8/1997 | Vermeer ................ 424/70.24 |
| 5,661,118 A | * | 8/1997 | Cauwet et al. ........... 510/124 |
| 5,830,438 A | * | 11/1998 | Dupuis ................... 424/45 |
| 5,882,660 A | * | 3/1999 | Chambers et al. ........ 424/401 |
| 5,972,920 A | * | 10/1999 | Seidel .................. 514/171 |
| 5,998,395 A | * | 12/1999 | Kligman ................ 514/171 |
| 6,001,885 A | | 12/1999 | Vega |
| 6,033,647 A | | 3/2000 | Touzan |
| 6,093,745 A | * | 7/2000 | Hammes et al. .......... 514/634 |
| 6,106,848 A | * | 8/2000 | Preuilh et al. ........... 424/401 |
| 6,132,746 A | * | 10/2000 | Hasenoehrl et al. ...... 424/402 |
| 6,146,664 A | * | 11/2000 | Siddiqui ................ 424/489 |
| 6,153,208 A | * | 11/2000 | McAtee et al. .......... 424/402 |
| 6,159,485 A | * | 12/2000 | Yu et al. ............... 424/401 |
| 6,190,678 B1 | * | 2/2001 | Hasenoehrl et al. ...... 424/401 |
| 6,231,837 B1 | * | 5/2001 | Stroud et al. ............ 424/59 |
| 6,248,749 B1 | | 6/2001 | Demarchez |
| 6,730,288 B1 | | 5/2004 | Abram |
| 7,029,659 B2 | | 4/2006 | Abram |
| 7,078,058 B2 | | 7/2006 | Jones |

FOREIGN PATENT DOCUMENTS

| EP | 0 539 215 A1 | 4/1993 |
| GB | 1 476 717 | 1/1976 |
| JP | 07187946 A * | 7/1995 |
| WO | 93/10754 | 6/1993 |
| WO | 93/10756 | 6/1993 |
| WO | 96/01632 | 1/1996 |
| WO | 96/17916 | 6/1996 |
| WO | 96/27376 | 9/1996 |
| WO | 9627376 | 9/1996 |
| WO | 96/37591 | 11/1996 |
| WO | 97/03648 | 2/1997 |
| WO | 97/27835 | 9/1997 |
| WO | 98/00499 | 1/1998 |

OTHER PUBLICATIONS

The Handbook of Cosmetic Science and Technology, Elsevier Science Publishers LTD, 1993. pp. 222-224.*
JP10114619 (Mar. 2000) Corresponds to USP 6,033,647).
JP-01-199916 (Aug. 11, 1989) (English Abstract).
Fragrance Journal, Apr. 1996, pp. 34-41, Fragrance Journal Company (English Abstract).
Abstract of 61-83946.
"FDA Approves Olux (Clobetasol Propionate) Foam For Scalp Dermatoses" http://www.pslgroup.com/dg/1D4096.htm, Doctor's Guide, May 31, 2000 (printed Feb. 26, 2007).
"DAIVONEX" Information for Health Professionals—Data Sheet, printed Nov. 1, 2006 from URL www.medsafe.givt.nz/profs/datasheet/d/Daivonexoint.htm.
"Clobetasol propionate" printed Nov. 1, 2006 from URL http://en.wikipedia.org/wiki/Clobetasol_propionate.
Clobex® Shampoo insert "Oct. 13, 2004" printed from http://www.clobex.com/PCLOBEX_SHAMPOO.pdf Feb. 26, 2007.
Abstract of FR 2718961, published Oct. 30, 1996.
Schrader, Dritter Teil 2. Haarkosmetika, 1989, pp. 680-709.

* cited by examiner

*Primary Examiner*—Sreeni Padmanabhan
*Assistant Examiner*—Renee Claytor
(74) *Attorney, Agent, or Firm*—Nixon & Vanderhye P.C.

(57) ABSTRACT

The invention concerns a foaming composition for washing and treating hair and/or scalp essentially characterized in that it contains in an aqueous medium: at least an active principle selected among corticoids and retinoids; at least an anionic surfactant; at least an amphoteric surfactant; and a pro-penetrating agent.

1 Claim, No Drawings

FOAMING COMPOSITION FOR WASHING AND TREATING HAIR AND/OR SCALP BASED ON AN ACTIVE PRINCIPLE

This is a continuation of PCT application No. PCT/FR99/01452, filed 17 Jun. 1999, the entire content of which is hereby incorporated by reference in this application.

The present invention relates to novel foaming compositions for washing and treating the hair and/or scalp, comprising at least one active principle chosen from corticosteroids and retinoids, one anionic surfactant, one amphoteric surfactant and one propenetrating agent, and to the treatment process employing such compositions.

Psoriasis is one of the commonest skin ailments among all chronic skin diseases. This disease is found in 1.4 to 2.9% of the population. The scalp is one of the favored sites for psoriasis; the latter causes essentially erythemas, desquamations, hyperkeratoses or pruritides and can also be responsible for a reduction in hair density. The treatments used to date involve salicylic acid, local steroids, anthralin, or coal or wood tar. These treatments are unpleasant, in particular when tar is applied, and require lengthy applications, in particular when hair ointments are used.

For the purpose of improving the quality of life for the patient, without however decreasing the therapeutic effect of the treatment, foaming compositions comprising corticosteroids have been developed. More particularly, the application time of these foaming compositions is reduced with respect to the conventional treatment.

Patent BE 84515 discloses a composition comprising hydrocortisone in a solvent mixture composed of 15 to 60% of aliphatic alcohol, 15 to 60% of propylene glycol and of 5 to 60% of a third solubilizing agent taken from the group consisting of 2-hydroxyethyl salicylate, dipropyl ketone and dimethylcocobenzylammonium chloride.

Patent EP 0 325 949 discloses a solution comprising at least 2.5% of corticosteroids, from 25 to 80% of a nonionic surfactant, from 0 to 70% of ethanol, from 0 to 70% of propylene glycol and an antimicrobial agent.

Nevertheless, the solvents present in these compositions have a tendency to evaporate very rapidly. Furthermore, the fluidity of these compositions renders the application difficult and it is often necessary to apply these compositions by rubbing in order to allow effective penetration of the active principles, the consequence of which is to irritate the epidermis even more, or to apply these compositions and to allow them to act for several hours, which is annoying to the patient.

To avoid evaporation of the solvent, provision has been made, in Patent WO 9627376, for a foam comprising a corticosteroid, a foam-breaking agent, a propellant and buffer. The foam-breaking agent is composed of an aliphatic alcohol, of water, of a fatty alcohol and of a nonionic surfactant. Nevertheless, when these foams are applied to keratinous fibers, their resulting esthetic appearance is not satisfactory and the scalp lying under the keratinous fibers may be insufficiently treated.

The Applicant Company has looked for compositions which do not exhibit the abovementioned disadvantages, that is to say a composition which makes it possible to improve the penetration of the active principle while being particularly easy to use and exhibiting good cosmetic properties.

The Applicant Company has now developed a foaming composition which exhibits the properties mentioned above.

The compositions of the present invention, while making possible good penetration of the active principles, also exhibit an improvement in the cosmetic performances of the compositions for the treatment of skin ailments or of the hair, the compositions of the invention leaving the hair soft and manageable and not rendering it greasy. Furthermore, these compositions are easy to rinse out.

The Applicant Company has also found that the foaming compositions of the present invention surprisingly make it possible to obtain a foam which exhibits improved characteristics of volume and of compactness with respect to the foaming compositions for the treatment of skin ailments or of the scalp of the prior art.

It has also been found that, surprisingly, the compositions which are subject matters of the present invention are stable over time, making it possible to prevent the precipitation of the active principles, and thus remain clear.

One of the subject matters of the invention is thus composed of a foaming composition for washing and treating the hair and/or the scalp.

Another subject matter of the invention is a process for washing and treating the hair and/or the scalp employing such a composition.

A subject matter of the invention is also a composition according to the invention for its application as medicament.

A subject matter of the invention is also the use of the compositions of the invention as medicament and for the manufacture of a medicament intended to treat skin ailments or hair.

Other subject matters of the invention will become apparent on reading the description and the examples which follow.

The foaming composition for washing and treating the hair and/or the scalp is essentially characterized in that it comprises, in an aqueous medium:
- at least one active principle chosen from corticosteroids and retinoids,
- at least one anionic surfactant,
- at least one amphoteric surfactant, and
- at least one propenetrating agent.

In the context of the present invention, the corticoids can be chosen from alclometasone dipropionate, amcinonide, beclomethasone dipropionate, betamethasone benzoate, betamethasone dipropionate, betamethasone valerate, budesonide, clobetasol propionate, preferably clobetasol 17-propionate, clobetasol butyrate, desonide, desoximetasone, dexamethasone, diflorasone diacetate, diflucortolone valerate, flurandrenolone, fluprednidene acetate, fluocortolone, fluocortin butyl, fluocinonide, fluocinolone acetonide, fluclorolone acetonide, flumetasone pivalate, feudiline hydrochloride, flumetholone, halcinonide, hydrocortisone, hydrocortisone acetate, hydrocortisone butyrate, hydrocortisone valerate, methylprednisolone acetate, mometasone furoate, methylprednisolone, prednisolone or triamcinolone acetonide or from pharmaceutically acceptable mixtures of the latter.

The retinoids can be chosen from all-trans-retinoic acid, also known as tretinoin or vitamin A acid, adapalene, isotretinoin, retinol, that is to say vitamin A, and its derivatives, such as retinol acetate, palmitate or propionate, motretinide, etretinate, acitretin, zinc all-trans-retinoate, third generation retinoids obtained by the addition of cyclic groups to the polyene side chain, also known as arotinoids, or synthetic retinoids, or from pharmaceutically acceptable mixtures of the latter.

Preference is given, among the retinoids, to adapalene, 4-[7-(1-adamantyl)-6-methoxyethoxymethoxy-2-naphthyl] benzoic acid, 2-hydroxy-4-[3-oxo-3-(3-tert-butyl-4-methoxyphenyl)-1-propynyl]benzoic acid and 4-(3,5,5,8,8,-pentamethyl-5,6,7,8-tetrahydro-2-naphthylthio)benzoic acid.

The active principle which is particularly preferred among the corticoids is clobetasol 17-propionate.

The active principle can be used in proportions of 0.001 to 5%, preferably between 0.01 to [sic] 0.3% and more preferably between 0.05 and 0.1% by weight with respect to the total weight of the composition.

In the context of the present invention, the nature of the anionic surfactants does not assume a really critical character.

Thus, mention may in particular be made, by way of example of anionic surfactants which can be used, alone or mixed, of the salts (in particular alkali metal, especially sodium, salts, ammonium salts, amine salts, aminoalcohol salts or magnesium salts) of the following compounds: alkyl sulfates, alkyl ether sulfates, alkylamido ether sulfates, alkylaryl polyether sulfates, monoglyceride sulfates, alkyl sulfonates, alkyl phosphates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkylsulfosuccinamates, alkyl sulfoacetates, alkyl ether phosphates, acylsarcosinates, acylisethionates and N-acyltaurates, the alkyl or acyl radical of these various compounds preferably comprising from 12 to 20 carbon atoms and the aryl radical preferably denoting a phenyl or benzyl group.

Mention may also be made, among the anionic surfactants which can further be used, of the salts of fatty acids, such as the salts of oleic, ricinoleic, palmitic and stearic acids, the acids of coconut oil or of hydrogenated coconut oil, or acyllactylates, the acyl radical of which comprises 8 to 20 carbon atoms. Use may also be made of weakly anionic surfactants, such as alkyl D-galactosideuronic acids and their salts, as well as polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$) alkylamido ether carboxylic acids and their salts, in particular those comprising from 2 to 50 ethylene oxide groups, and their mixtures.

Among the anionic surfactants, it is preferable to use, according to the invention, alkyl sulfate or alkyl ether sulfate salts or their mixtures.

More particularly, it is preferable to use sodium lauryl ether sulfate (2 mol EO), in particular that sold under the name "Texapon N70®", sodium lauryl ether sulfate, particularly that sold under the name "Sipon AOS 225 UP®", and sodium lauryl sulfate, in particular that sold under the name "Texapon K 12®".

These anionic surfactants can be used in proportions of between 0.05 and 50%, preferably between 1 and 30% and more preferably between 2 and 25% of Active Material (A.M.) by weight with respect to the total weight of the composition.

The amphoteric surfactants, the nature of which does not assume a critical character in the context of the present invention, may be in particular derivatives of aliphatic secondary or tertiary amines in which the aliphatic radical is a linear or branched chain comprising 8 to 22 carbon atoms and comprising at least one water-solubilizing anionic group (for example carboxylate, sulfonate, sulfate, phosphate or phosphonate); mention may also be made of ($C_8$-$C_{20}$)alkyl betaines, sulfobetaines, ($C_8$-$C_{20}$)alkyl amido($C_1$-$C_6$)alkyl betaines or ($C_8$-$C_{20}$)alkyl amido($C_1$-$C_6$)alkyl sulfobetaines.

Mention may be made, among the amine derivatives, of the products sold under the Miranol names, as disclosed in U.S. Pat. Nos. 2,528,378 and 2,781,354 and with structures:

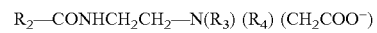

in which: $R_2$ denotes an alkyl radical derived from an acid $R_2$—COOH present in hydrolyzed coconut oil or a heptyl, nonyl or undecyl radical, $R_3$ denotes a beta-hydroxyethyl group and $R_4$ denotes a carboxymethyl group;

in which:
B represents —$CH_2CH_2OX'$, C represents —$(CH_2)_z$—Y', with z=1 or 2,
X' denotes the —$CH_2CH_2$—COOH group or a hydrogen atom
Y' denotes —COOH or the —$CH_2CHOH$—$SO_3H$ radical
$R_5$ denotes an alkyl radical of an acid $R_9$—COOH present in hydrolyzed linseed oil or coconut oil, an alkyl radical, in particular a $C_7$, $C_9$, $C_{11}$ or $C_{13}$ radical, a $C_{17}$ alkyl radical and its iso form, or an unsaturated $C_{17}$ radical.

These compounds are classified in the CTFA dictionary, 7th Edition, 1998, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Lauroamphodipropionic Acid and Cocoamphodipropionic Acid.

Among the amphoteric surfactants, corobetaines are particularly preferred and more particularly cocamidopropyl betaine, in particular that sold under the name "Tegobetaine F50®", cocamidopropyl hydroxysultaine, in particular that sold under the name "Amonyl 675 SB®", and cocoyl betaines, in particular those sold under the names "Dehyton AB 30®" and "Chimexane HC®".

These amphoteric surfactants can be used in proportions of between 0.01 and 30%, preferably between 0.5 and 20% and more preferably between 1 and 15% as A.M. by weight with respect to the total weight of the composition.

The ratio of the proportion as A.M. of the anionic surfactants to the proportion as A.M. of the amphoteric surfactants is preferably between 1 and 20 and more preferably between 2 and 10.

The propenetrating agent, which makes it possible to facilitate the penetration of the active principles, preferably dissolves the active principle present in the composition according to the invention. More particularly, it is chosen from volatile $C_1$-$C_4$ alcohols, such as ethanol or isopropanol, from polyhydric alcohols, such as propylene glycol, and from glycol ethers, such as ethoxydiglycol.

The preferred propenetrating agent in the context of the present invention is ethanol.

The propenetrating agents can be used in concentrations of between 0.1 and 25% and preferably of between 5 and 10% by weight with respect to the total weight of the composition.

The ratio of the proportion as A.M. of the anionic surfactants to the proportion of the propenetrating agents is preferably between 0.1 and 10 and more preferably between 0.5 and 5 and more preferably still between 1 and 2.

The compositions which are subject matters of the present invention can be thickened and their cosmetic properties improved by adding thereto, for example, cationic polymers, acrylic polymers or cellulose derivatives which are or are not quaternized.

The cationic polymers which can be used in accordance with the present invention can be chosen from all those already known per se as improving the cosmetic properties of hair treated with detergent compositions, namely, in particular, those disclosed in Patent Application EP-A 0,337, 354 and in French Patent Applications FR-A-2,270,846, 2,383,660, 2,598,611, 2,470,596 and 2,519,863.

More generally still, within the meaning of the present invention, the expression "cationic polymer" denotes any polymer comprising cationic groups and/or groups which can be ionized to cationic groups.

The preferred cationic polymers are chosen from those which comprise units comprising primary, secondary, tertiary and/or quaternary amine groups, which can either form part of the main polymer chain or be carried by a side substituent directly connected to the latter.

The cationic polymers used generally have a number molecular mass of between 500 and 5 H $10^6$ approximately and preferably of between $10^3$ and 3 H $10^6$ approximately.

Mention may more particularly be made, among cationic polymers, of quaternized proteins (or protein hydrolysates) and polymers of the polyamine, polyaminoamide and poly (quaternary ammonium) type. These are known products.

The quaternized proteins or protein hydrolysates are in particular chemically modified polypeptides carrying quaternary ammonium groups at the chain end or grafted onto the chain. Their molecular mass can vary, for example, from 1500 to 10,000 and in particular from 2000 to 5000 approximately. Mention may in particular be made, among these compounds, of:

collagen hydrolysates carrying triethylammonium groups, such as the products sold under the name "Quat-Pro E" by Maybrook and called, in the CTFA dictionary, "Triethonium Hydrolyzed Collagen Ethosulfate";

collagen hydrolysates carrying trimethylammonium and trimethylstearylammonium chloride groups, sold under the name of "Quat-Pro S" by Maybrook and called, in the CTFA dictionary, "Steartrimonium Hydrolyzed Collagen";

animal protein hydrolysates carrying trimethylbenzylammonium groups, such as the products sold under the name "Crotein BTA" by Croda and called, in the CTFA dictionary, "Benzyltrimonium Hydrolyzed Animal Protein";

protein hydrolysates carrying, on the polypeptide chain, quaternary ammonium groups comprising at least one alkyl radical having from 1 to 18 carbon atoms.

Mention may be made, among these protein hydrolysates, inter alia, of:

"Croquat L", the quaternary ammonium groups of which comprise a $C_{12}$ alkyl group;

"Croquat M", the quaternary ammonium groups of which comprise $C_{10}$-$C_{18}$ alkyl groups;

"Croquat S", the quaternary ammonium groups of which comprise a $C_{18}$ alkyl group;

"Crotein Q", the quaternary ammonium groups of which comprise at least one alkyl group having from 1 to 18 carbon atoms.

These various products are sold by Croda.

Other quaternized proteins or hydrolysates are, for example, those corresponding to the formula:

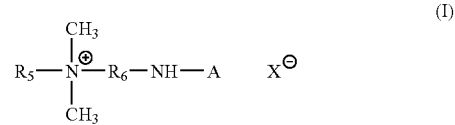

(I)

in which $X^-$ is an anion of an organic or inorganic acid, A denotes a protein residue derived from collagen protein hydrolysates, $R_5$ denotes a lipophilic group comprising up to 30 carbon atoms and $R_6$ represents an alkylene group having 1 to 6 carbon atoms. Mention may be made, for example, of the products sold by Inolex under the name "Lexein QX 3000", called "Cocotrimonium Collagent [sic] Hydrolysate" in the CTFA dictionary.

Mention may also be made of quaternized plant proteins, such as wheat, maize or soya proteins: mention may be made, as quaternized wheat proteins, of those sold by Croda under the names "Hydrotriticum WQ or QM", called "Cocodimonium Hydrolysed Wheat Protein" in the CTFA dictionary. "Hydrotriticum QL", called "Laurdimonium Hydrolysed Wheat Protein" in the CTFA dictionary or "Hydrotriticum QS", called "Steardimonium Hydrolysed Wheat Protein" in the CTFA dictionary.

The polymers of the polyamine, polyamidoamide or poly (quaternary ammonium) type which can be used in accordance with the present invention which can be mentioned in particular are those disclosed in French Patents No. 2,505, 348 or 2,542,997. Mention may be made, among these polymers, of:

(1) optionally quaternized vinyl-pyrrolidone/dialkylaminoalkyl acrylate α-methacrylate [sic] copolymers, such as the products sold under the name "Gafquat" by ISP, such as, for example, Gafquat 734, 755 or H5100, or else the product called "Copolymer 937". These polymers are disclosed in detail in French Patents 2,077,143 and 2,393,573.

(2) cellulose ether derivatives comprising quaternary ammonium groups disclosed in French Patent 1,492,597 and in particular the polymers sold under the names "JR" (JR 400, JR 125, JR 30M) or "LR" (LR 400, LR 30M) by Union Carbide Corporation. These polymers are also defined in the CTFA dictionary as quaternary ammoniums of hydroxyethylcellulose which has reacted with an epoxide substituted by a trimethylammonium group.

(3) cationic cellulose derivatives, such as the copolymers of cellulose or the cellulose derivatives grafted with a water-soluble quaternary ammonium monomer and disclosed in particular in U.S. Pat. No. 4,131,576, such as hydroxyalkyl celluloses, for example hydroxymethyl-, hydroxyethyl- or hydroxypropyl-celluloses, grafted in particular with a methacryloylethyltrimethylammonium, methacrylmidopropyltrimethylammonium or dimethyldiallylammonium salt.

The marketed products corresponding to this definition are more particularly the products sold under the name "Celquat SC 240", "Celquat L 200" and "Celquat M 100" by National Starch.

(4) the cationic polysaccharides disclosed more particularly in U.S. Pat. Nos. 3,589,578 and 4,031,307, such as guar gums comprising cationic trialkylammonium groups. Use is made, for example, of guar gums modified by a 2,3-epoxypropyltrimethylammonium salt (for example, chloride).

Such products are sold in particular under the trade names of Jaguar C13 S, Jaguar C15, Jaguar C17 or Jaguar C162 by Meyhall.

(5) polymers composed of piperazinyl units and of divalent, straight- or branched-chain alkylene or hydroxyalkylene radicals, optionally interrupted by oxygen, sulfur or nitrogen atoms or by aromatic or heterocyclic rings, as well as the oxidation and/or quaternization products of these polymers. Such polymers are disclosed in particular in French Patents 2,162,025 and 2,280,361.

(6) water-soluble polyaminoamides prepared in particular by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epilhalohydrin, a diepoxide or a bisunsaturated derivative; crosslinking agent being used in proportions ranging from 0.025 to 0.35 mol per amine group of the polyaminoamide; these polyaminoamides can be alkylated or, if they comprise one or more tertiary amine functional groups, quaternized. Such polymers are disclosed in particular in French Patents 2,252,840 and 2,368,508.

(7) polyaminoamide derivatives resulting from the condensation of polyalkylenepolyamines with polycarboxylic acids, followed by an alkylation by bifunctional agents. Mention may be made, for example, of adipic acid/diakylaminohydroxyalkyldialylenetriamine polymers in which the alkyl radical comprises from 1 to 4 carbon atoms and preferably denotes methyl, ethyl or propyl. Such polymers are disclosed in particular in French Patent 1,583,363.

Mention may more particularly be made, among these derivatives, of the adipic acid/dimethylaminohydroxypropyl/diethylenetriamine polymers sold under the name "Cartaretine F, F4 or F8" by Sandoz.

(8) polymers obtained by reaction of a polyalkylenepolyamine comprising two primary amine groups and at least one secondary amine group with a dicarboxylic acid chosen from diglycolic acid and saturated aliphatic dicarboxylic acids having from 3 to 8 carbon atoms. The molar ratio of polyalkylenepolylamine to dicarboxylic acid being between 0.8:1 and 1.4:1; the polyaminoamide resulting therefrom being brought to react with epichlorohydrin in a molar ratio of epichlorohydrin in relation to the secondary amine group of the polyaminoamide of between 0.5:1 and 1.8:1. Such polymers are disclosed in particular in U.S. Pat. Nos. 3,227,615 and 2,961,347.

Polymers of this type are in particular sold under the name "Hercosett 57" by Hercules Inc. or else under the name of "PD 170" or "Delsette 101" by Hercules in the case of the adipic acid/epoxypropyl/diethylenetriamine [sic] copolymer.

(9) cyclohomopolymers of methyldiallylamine or of dimethyldiallylammonium, such as the homopolymers comprising, as main constituent of the chain, units corresponding to the formulae (VI) or (VI'):

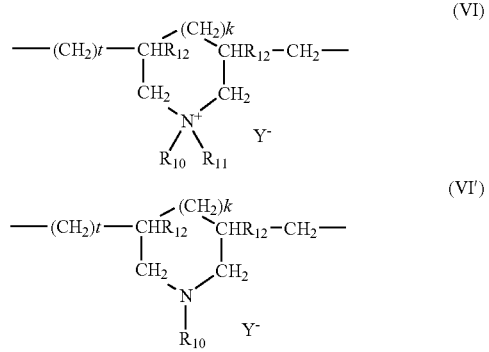

in which formulae k and t are equal to 0 or 1, the sum k+t being equal to 1; $R_{12}$ denotes a hydrogen atom or a methyl radical; $R_{10}$ and $R_{11}$, independently of one another, denote an alkyl group having from 1 to 22 carbon atoms, a hydroxyalkyl group in which the alkyl group preferably has 1 to 5 carbon atoms or a lower amidoalkyl group or $R_{10}$ and $R_{11}$ can denote, jointly with the nitrogen atom to which they are attached, heterocyclic group, such as piperidinyl or morpholinyl; $Y^-$ is an anion, such as bromide, chloride, acetate, borate, citrate, tartrate, bisulfate, bisulfite, sulfate or phosphate. These polymers are disclosed in particular in French Patent 2,080,759 and in its Certificate of Addition 2,190,406.

Mention may more particularly be made, among the polymers defined above, of the dimethyldiallylammonium chloride homopolymer sold under the name "Merquat 100" by Merck.

(10) the quaternary diammonium polymer comprising repeat units corresponding to the formula:

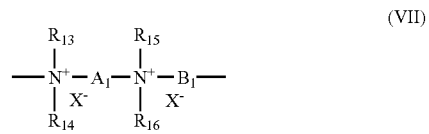

in which formula (VII):

$R_{13}$, $R_{14}$, $R_{15}$ and $R_{16}$, which are identical or different, represent aliphatic, alicyclic or arylaliphatic radicals comprising from 1 to 20 carbon atoms or lower hydroxyalkyl aliphatic radicals or else $R_{13}$, $R_{14}$, $R_{15}$ and $R_{16}$, together or separately, form, with the nitrogen atoms to which they are attached, heterocycles optionally comprising a second heteroatom other than nitrogen or else $R_{13}$, $R_{14}$, $R_{15}$ and $R_{16}$ represent a linear or branched $C_1$-$C_6$ alkyl radical substituted by a nitrile, ester, acyl, amide or —CO—O—$R_{17}$—D or —CO—NH—$R_{17}$—D group, where $R_{17}$ is an alkylene and D a quaternary ammonium group; $A_1$ and $B_1$ represent polymethylene groups comprising from 2 to 20 carbon atoms which can be linear or branched and saturated or unsaturated, and which can comprise, bonded to or inserted into the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid; $A_1$, $R_{13}$ and $R_{15}$ can form, with the two nitrogen atoms to which they are attached, a piperazine ring, in addition, if $A_1$ denotes a linear or branched, saturated or unsaturated alkylene or hydroxyalkylene radical, $B_1$ can also denote a $(CH_2)_n$—CO—D—OC—$(CH_2)_n$ group in which D denotes:

a) a glycol residue of formula: —C—Z—O—, where Z denotes a linear or branched hydrocarbon-comprising radical or a group corresponding to one of the following formulae:

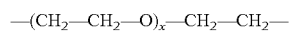

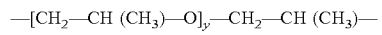

where x and y denote an integer from 1 to 4, representing a defined and unique degree of polymerization, or any number from 1 to 4 representing a mean degree of polymerization;

b) a bis-secondary diamine residue, such as a piperazine derivative;

c) a bis-primary diamine residue of formula: —NH—Y—NH—, where Y denotes a linear or branched hydrocarbon-comprising radical or else the divalent radical —$CH_2$—$CH_2$—S—S—$CH_2$—$CH_2$—;

d) a ureylene group of formula: —NH—CO—NH—; preferably, X⁻ is an anion, such as chloride or bromide.

These polymers have a number [lacuna] molecular mass generally of between 1000 and 100,000.

Polymers of this type are disclosed in particular in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) polymers of poly(quaternary ammonium) composed of units of formula (VIII):

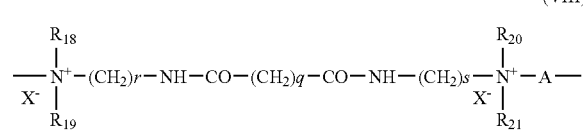

in which formula:

$R_{18}$, $R_{19}$, $R_{20}$ and $R_{21}$, which are identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer of between 1 and 6, with the proviso that $R_{18}$, $R_{19}$, $R_{20}$ and $R_{21}$ do not simultaneously represent a hydrogen atom, r and s, which are identical or different, are integers of between 1 and 6, q is equal to 0 or to an integer of between 1 and 34, X denotes a halogen atom, A denotes a radical from a dihalide or preferably represents —CH$_2$CH$_2$—O—CH$_2$—CH$_2$—.

Such compounds are disclosed in particular in Patent Application EP-A-122,324.

Mention may be made among these, for example, of the products "Mirapol A 15", "Mirapol AD1", "Mirapol AZ1" and "Mirapol 175", sold by Miranol.

(12) homopolymers or copolymers derived from acrylic or methacrylic acids and comprising units:

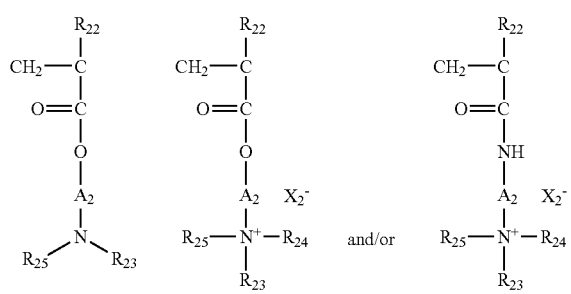

in which the $R_{22}$ groups independently denote H or CH$_3$, the $A_1$ groups independently denote a linear or branched alkyl group of 1 to 6 carbon atoms or a hydroxyalkyl group of 1 to 4 carbon atoms, the $R_{23}$, $R_{24}$ and $R_{25}$ groups, which are identical or different, independently denote an alkyl group of 1 to 18 carbon atoms or a benzyl radical, the $R_{26}$ and $R_{27}$ groups represent a hydrogen atom or an alkyl group of 1 to 6 carbon atoms, $X_2^-$ denotes an anion, for example methyl sulfate or halide, such as chloride or bromide.

The comonomer or comonomers which can be used in the preparation of the corresponding copolymers belong to the family of acrylamides, methacrylamides, diacetone acrylamides, acrylamides and methacrylamides substituted at the nitrogen by lower alkyls, alkyl esters, of acrylic or methacrylic acids, vinylpyrrolidone or vinyl esters.

(13) quaternary polymers of vinylpyrrolidone and of vinylimidazole, such as, for example, the products sold under the names Luviquat FC 905, FC 550 and FC 370 by B.A.S.F.

(14) polyamines, such as Polyquart H sold by Henkel, referenced under the name "Polyethylene Glycol (15) Tallow Polyamine" in the CTFA dictionary.

(15) crosslinked polymers of methacryloyloxyethyltrimethylammonium chloride, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, in particular methylenebisacrylamide. Use may more particularly be made of a crosslinked acrylamide/methacryloyloxyethyltrimethylammonium chloride (20/80 by weight) copolymer in the form of a dispersion comprising 50% by weight of the said copolymer in mineral oil. This dispersion is sold under the name of "Salcare SC 92" by Allied Colloids. Use may also be made of a crosslinked homopolymer of methacryloyloxyethyltrimethylammonium chloride comprising approximately 50% by weight of the homopolymer in mineral oil. This dispersion is sold under the name of "Salcare SC 95" by Allied Colloids.

Other cationic polymers which can be used in the context of the invention are polyalkyleneimines, in particular polyethyleneimines, polymers comprising vinylpyridine or vinylpyridinium units, condensates of polyamines and of epichlorohydrin, quaternary polyureylenes and chitin derivatives.

According to the invention, use may more particularly be made of polymers chosen from Mirapol, the compound of formula (VII) in which $R_{13}$, $R_{14}$, $R_{15}$ and $R_{16}$ represent the methyl radical, $A_1$ represents the radical of formula —(CH$_2$)$_3$— and $B_1$ represents the radical of formula —(CH$_2$)$_6$— and X⁻ represents the chloride anion (subsequently referred to as Mexomere PO) and the compound of formula (VII) in which $R_{13}$ and $R_{14}$ represent the ethyl radical. $R_{15}$ and $R_{16}$ represent the methyl radical, $A_1$ and $B_1$ represent the radical of formula —(CH$_2$)$_3$— and X⁻ represents the bromide anion (subsequently referred to as Mexomere PAK).

Preference is given, among all the cationic polymers which can be used, to the use of the compounds described above in points (3) and (4).

According to the invention, the cationic polymer or polymers can represent from 0.001% to 10% by weight, preferably from 0.005% to 5% by weight and more preferably still from 0.01% to 3% by weight of the total weight of the final composition.

The aqueous medium can comprise, in addition to water, cosmetically acceptable solvents other than the propenetrating agent, such as monoalcohols, polyalcohols or glycol ethers, used alone or as a mixture.

Mention may more particularly be made, among these solvents, of polyethylene glycol, glycerol and sorbitol. The solvents are preferably used in proportions of 0.5 to 10% by weight with respect to the total weight of the composition.

The pH of the compositions is preferably between 2 and 9 and in particular between 3 and 8. For clobetasol propionate, the pH is advantageously between 5.5 and 6.5. It is adjusted with cosmetically acceptable basifying or acidifying agents.

The compositions according to the invention can additionally comprise other adjuvants used in foaming compositions, such as shampoos, and in particular ceramides, such as those disclosed in French Patent FR 2 673 179, glycoceramides, or well-known nonionic surfactants which can be chosen from polyethoxylated, polypropoxylated or polyglycerolated alcohols, α-diols, alkylphenols or fatty acids with a fatty chain comprising, for example, 8 to 18 carbon atoms, it being possible for the number of ethylene oxide and propylene oxide groups to range in particular from 2 to 50 and it being possible for the number of glycerol groups to range in particular from 2 to 30. Mention may also be made of copolymers of ethylene oxide and of propylene oxide or condensates of ethylene oxide and of propylene oxide with fatty alcohols; polyethoxylated fatty amides preferably having 2 to 30 mol of ethylene oxide or polyglycerolated fatty amides comprising on average 1 to 5 glycerol groups and in particular 1.5 to 4 glycerol groups; polyethoxylated fatty amines preferably having 2 to 3 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglycamine derivatives, or amine oxides, such as ($C_{10}$-$C_{16}$)alkylamine oxides or N-acrylaminopropylmorpholine oxides. Alkylpolyglycosides and polyglycerolated alcohols, α-diols, alkylphenols or of [sic] fatty acids are more particularly preferred.

The compositions can also comprise thickening agents chosen in particular from sodium alginate, gum arabic, cellulose derivatives, such as methylcellulose, hydroxymethylcellulose, hydroxyethylcellulose, hydroxylpropylcellulose or hydroxypropylmethylcellulose, guar gum or its derivatives, xanthan gums, scleroglucans, crosslinked polyacrylic acids, polyurethanes, copolymers based on maleic acid or anhydride, or associative thickeners carrying fatty chains of natural type, such as the product sold under the name Natrasol Plus, or synthetic type, such as the products sold under the name Pemulen.

The thickener can also be obtained by mixing polyethylene glycol and polyethylene glycol stearates or distearates or mixing amides and phosphoric esters.

The compositions in accordance with the invention can also comprise colorants, viscosity-modifying agents, pearlescent agents, moisturizing agents, antidandruff agents, antiseborrheic agents, sunscreens, proteins, vitamins, α-hydroxy acids, salts, fragrances, preservatives, sequestering agents, softeners, foam modifiers, detoxifying agents or their mixtures.

Conditioning agents can also be used, such as hydrogenated or nonhydrogenated and synthetic or nonsynthetic natural hydrocarbonaceous oils which are cyclic or aliphatic and linear or branched (saturated or unsaturated), volatile or nonvolatile, organomodified or nonorganomodified and soluble or insoluble silicones, perfluorinated or fluorinated oils, polybutenes and polyisobutenes, fatty esters which are provided in a liquid, pasty or solid form, esters of polyhydric alcohols, glycerides, natural or synthetic waxes, silicon gums and resins, quaternary ammonium salts, such as, for example, the compound classified in the CTFA dictionary, 7th Edition, 1998, under the name Quaternium-22 and sold under the name "Ceraphyl 60", or the mixture of these various agents.

In the context of the present invention, the compositions are more particularly in the form of liquids, optionally thickened liquids.

They can be used as they are or can be diluted before use.

The compositions in accordance with the invention are more particularly used as shampoos for treating the hair or the scalp.

In this case, the composition is preferably applied to wet or dry hair, gently massaging is then carried out, during which a foam is formed, rinsing is then carried out and, optionally, the shampoo is applied a further time, followed by a further rinsing with water.

A subject matter of the invention is consequently a foaming composition as defined above for its application as medicament.

Another subject matter of the present invention is the use of a composition as defined above in the manufacture of a medicament intended for the treatment of ailments of the scalp.

The compositions according to the invention are very particularly indicated in the treatment of eczemas, eczematous or psoriatic erythrodermas, pruriginous lesions, chronic lupus erythematosus, psoriasis and parapsoriasis en plaque.

These treatments generally require an application as described above 2 to 3 times per week.

Several examples of compositions according to the invention will now be given by way of illustration and without any limiting nature.

EXAMPLE I

The following shampoo is prepared:

| | |
|---|---|
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Transcutol ® (ethoxydiglycol) | 10 g |
| Clobetasol propionate | 0.05 g |
| Jaguar C162 ® (hydroxypropylguar hydroxypropyltrimonium chloride | 0.5 g |
| Lactic acid | q.s. pH 6 |
| Demineralized water | q.s. 100 g |

EXAMPLE II

The following shampoo is prepared:

| | |
|---|---|
| Dehyton AB 30 (cocoyl betaine comprising 32% A.M.) | 6 g |
| Jaguar C162 ® (hydroxypropylguar hydroxypropyltrimonium chloride | 0.5 g |
| Sipon AOS 225 UP ® (sodium lauryl ether sulfate comprising 28% A.M.) | 43 g |
| Ethanol (95/96%) | 10 g |
| Clobetasol propionate | 0.05 g |
| Benzalkonium chloride | 0.005 g |
| Lactic acid | q.s. pH 6 |
| Demineralized water | q.s. 100 g |

EXAMPLE III

The following shampoo is prepared:

| | |
|---|---|
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Transcutol ® (ethoxydiglycol) | 10 g |
| Adapalene | 0.05 g |
| Jaguar C162 ® (hydroxypropylguar hydroxypropyltrimonium chloride | 0.5 g |
| Lactic acid | q.s. pH 6 |
| Demineralized water | q.s. 100 g |

EXAMPLE IV

The following shampoo is prepared:

| | |
|---|---|
| Sipon AOS 225 UP ® (sodium lauryl ether sulfate comprising 28% A.M.) | 43 g |
| Dehyton AB 30 (cocoyl betaine comprising 31% A.M.) | 6 g |
| Ethanol (95/96%) | 10 g |
| Benzalkonium chloride | 0.01 g |
| Jaquar C162 ® (hydroxypropylguar hydroxypropyltrimonium chloride | 0.5 g |
| Clobetasol propionate | 0.05 g |
| Lactic acid | q.s. pH 6 |
| Demineralized water | q.s. 100 g |

EXAMPLE V

The following shampoo is prepared:

| | |
|---|---|
| Celquat SC 240 ® (polyquaternium 10) | 2 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Citric acid•1H$_2$O | 0.24 g |
| Sodium citrate•2H$_2$O | 2.6 g |
| Ethanol (95/96%) | 10 g |
| Clobetasol propionate | 0.05 g |
| Demineralized water | q.s. 100 g |

EXAMPLE VI

The following shampoo is prepared:

| | |
|---|---|
| Celquat SC 240 ® (polyquaternium 10) | 2 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Ethanol (95/96%) | 10 g |
| Clobetasol propionate | 0.05 g |
| Demineralized water | q.s. for 100 g |

EXAMPLE VII

The following shampoo is prepared:

| | |
|---|---|
| Citric acid•1H$_2$O | 0.24 g |
| Sodium citrate•2H$_2$O | 2.6 g |
| Methyl para-hydroxybenzoate | 0.1 g |
| Celquat SC 240 ® (polyquaternium 10) | 2 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Clobetasol propionate | 0.05 g |
| Ethanol (95/96%) | 10 g |
| Purified water | q.s. for 100 g |

EXAMPLE VIII

The following shampoo is prepared:

| | |
|---|---|
| Citric acid | 0.24 g |
| Sodium citrate | 2.6 g |
| Celquat SC 240 ® (polyquaternium 10) | 2 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Clobetasol propionate | 0.05 g |
| Ethanol (95/96%) | 10 g |
| Purified water | q.s. for 100 g |

EXAMPLE IX

The following shampoo is prepared:

| | |
|---|---|
| Jaguar C162 ® (hydroxypropylguar hydroxypropyltrimonium chloride | 0.5 g |
| Chimexane HC (cocoyl betaine comprising 32% A.M.) | 6.0 g |
| Sipon AOS 225 UP ® (sodium lauryl ether sulfate comprising 28% A.M.) | 43.0 g |
| Ethanol (95/96%) | 10.0 g |
| Clobetasol propionate | 0.05 g |
| Rewoquat B50 ® (50% benzalkonium chloride) | 0.01 g |
| Purified water | q.s. for 100 g |

EXAMPLE X

The following shampoo is prepared:

| | |
|---|---|
| Jaguar C162 ® (hydroxypropylguar hydroxypropyltrimonium chloride | 0.5 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Ethanol (95/96%) | 10 g |
| Adapalene | 0.05 g |
| Demineralized water | q.s. for 100 g |

EXAMPLE XI

The following shampoo is prepared:

| | |
|---|---|
| Jaguar C162 ® (hydroxypropylguar hydroxypropyltrimonium chloride | 0.5 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Ethanol (95/96%) | 10 g |
| 4-[7-(1-Adamantyl)-6-methoxyethoxymethoxy-2-naphthyl]benzoic acid | 0.05 g |
| Demineralized water | q.s. for 100 g |

EXAMPLE XII

The following shampoo is prepared:

| | |
|---|---|
| Jaguar C162 ® (hydroxypropylguar hydroxypropyltrimonium chloride | 0.5 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Ethanol (95/96%) | 10 g |
| 2-Hydroxy-4-[3-oxo-3-(3-tert-butyl-4-methoxyphenyl)-1-propynyl]benzoic acid | 0.05 g |
| Demineralized water | q.s. for 100 g |

EXAMPLE XIII

The following shampoo is prepared:

| | |
|---|---|
| Jaguar C162 ® (hydroxypropylguar hydroxypropyltrimonium chloride | 0.5 g |
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Rewoquat B50 ® (50% benzalkonium chloride) | 0.01 g |
| Ethanol (95/96%) | 10 g |
| 4-(3,5,5,8,8-Pentamethyl-5,6,7,8-tetrahydro-2-naphthylthio)benzoic acid | 0.05 g |
| Demineralized water | q.s. for 100 g |

EXAMPLE XIV

The following shampoo is prepared:

| | |
|---|---|
| Texapon N70 ® (sodium lauryl ether sulfate (2 mol EO) comprising 70% A.M.) | 17 g |
| Dehyton AB 30 ® (cocoyl betaine comprising 32% A.M.) | 6 g |
| Methocel E4M (hydroxypropylmethylcellulose) | 1 g |
| Citric acid•1$H_2$O | 0.24 g |
| Sodium citrate•2$H_2$O | 2.6 g |
| Ceraphyl 60 (quaternium 22) | 0.5 g |
| Clobetasol propionate | 0.05 g |
| Ethanol (95/96%) | 10 g |
| Demineralized water | q.s. 100 g |

The compositions of Examples I to XIV above are stable on storage and exhibit a satisfactory foaming effect.

A clinical study, in which a composition according to Example IX was used as shampoo once daily for two weeks, the shampoo being applied to wet hair and left in contact for 10 minutes in order to be subsequently rinsed out, made it possible to observe in patients suffering from psoriasis a reduction on the scalp of erythemas of 37%, of desquamation of 47%, of hyperkeratoses of 50% and of pruritides of 57%.

What is claimed is:

1. A foaming composition for washing and treating the hair and/or the scalp consisting of 0.24 g citric acid, 2.6 g sodium citrate, 2 g polyquaternium 10, 17 g of sodium lauryl ether sulphate (2 moles of ethylene oxide, comprising 70% of active material), 6 g of cocoyl betaine (comprising 32% active material), 0.05 g clobetasol propionate, 10 g ethanol (95/96%), and q.s. for 100 g purified water.

\* \* \* \* \*